US00RE50815E

(19) United States
(12) Reissued Patent
Somareddy

(10) Patent Number: US RE50,815 E
(45) Date of Reissued Patent: Mar. 10, 2026

(54) SYSTEMS AND METHODS FOR NEURAL PATHWAYS CREATION/REINFORCEMENT BY NEURAL DETECTION WITH VIRTUAL FEEDBACK

(71) Applicant: Neuromersive, Inc., Fort Worth, TX (US)

(72) Inventor: Veena Somareddy, Euless, TX (US)

(73) Assignee: Neuromersive, Inc., Fort Worth, TX (US)

(21) Appl. No.: 18/625,758

(22) Filed: Apr. 3, 2024

Related U.S. Patent Documents

Reissue of:
(64) Patent No.: 11,210,961
Issued: Dec. 28, 2021
Appl. No.: 15/919,165
Filed: Mar. 12, 2018

(51) Int. Cl.
*G09B 5/02* (2006.01)
*A61B 5/24* (2021.01)
(Continued)

(52) U.S. Cl.
CPC ..... *G09B 5/02* (2013.01); *A61B 5/24* (2021.01); *A61B 5/375* (2021.01); *G06F 3/011* (2013.01);
(Continued)

(58) Field of Classification Search
CPC ..... G09B 23/28; G09B 23/30; G09B 23/32; G16H 20/00; G16H 20/30; A61B 5/24; A61B 5/742; A61B 5/7425; A61B 5/744; A61B 5/745; A61B 2505/09; G06F 3/01; G06F 3/011; G06F 3/015; G06F 3/016; A63B 24/0075
See application file for complete search history.

(56) References Cited

U.S. PATENT DOCUMENTS 5,999,895 A 12/1999 Forest
6,005,549 A 12/1999 Forest
(Continued)

OTHER PUBLICATIONS

International Search Report and Written Opinion issued for PCT Application No. PCT/US2019/021532, dated Jun. 6, 2019, 9 pages.
(Continued)

*Primary Examiner* — Joshua Kading
(74) *Attorney, Agent, or Firm* — Whitaker Chalk Swindle & Schwartz PLLC; Juan Vasquez

(57) ABSTRACT

The present disclosure relates to methods and systems for providing virtual feedback of a neural pattern to create a neural pathway corresponding to an action of an affected limb of a brain injury patient. Embodiments provide for detecting a neural pattern and determining a target action associated with the detected neural pattern. A virtual feedback is generated that includes a virtual action to be performed in a virtual representation of the affected limb. In embodiments, the brain injury may prevent the affected limb from performing the target action. The virtual representation of the affected limb is superimposed over a real-world presence of the affected limb such that the virtual representation is presented to the patient in lieu of the real-world presence, and the virtual action is performed in the virtual representation, such that the virtual action is presented to the patient in lieu of the target action in the real-world.

12 Claims, 4 Drawing Sheets

(AMENDED)

(51) Int. Cl.

| | |
|---|---|
| ***A61B 5/375*** | (2021.01) |
| ***G06F 3/01*** | (2006.01) |
| ***G06T 11/60*** | (2006.01) |
| ***G09B 19/00*** | (2006.01) |

(52) U.S. Cl.
CPC ..... *G06F 3/015* (2013.01); *G06T 11/60* (2013.01); *G09B 19/00* (2013.01); *A61B 2505/09* (2013.01)

(56) References Cited

U.S. PATENT DOCUMENTS

| | | | | |
|---|---|---|---|---|
| 6,106,437 | A | 8/2000 | Brooks | |
| 6,160,536 | A | 12/2000 | Forest | |
| 6,903,723 | B1 | 6/2005 | Forest | |
| 8,979,665 | B1 | 3/2015 | Najafi et al. | |
| 10,204,525 | B1 | 2/2019 | Tillis | |
| 2003/0120183 | A1 | 6/2003 | Simmons | |
| 2003/0210227 | A1 | 11/2003 | Smith | |
| 2004/0058780 | A1 | 3/2004 | Edgeton | |
| 2007/0016265 | A1* | 1/2007 | Davoodi | G09B 19/003 607/48 |
| 2007/0066918 | A1 | 3/2007 | Dewald et al. | |
| 2007/0282228 | A1 | 12/2007 | Einav et al. | |
| 2007/0282564 | A1 | 12/2007 | Sprague et al. | |
| 2008/0319252 | A1 | 12/2008 | Chapman et al. | |
| 2009/0147991 | A1 | 6/2009 | Chau | |
| 2010/0016730 | A1 | 1/2010 | Tanaka et al. | |
| 2010/0156653 | A1 | 6/2010 | Chaudhari et al. | |
| 2010/0260385 | A1 | 10/2010 | Chau | |
| 2010/0321286 | A1 | 12/2010 | Haggerty et al. | |
| 2011/0010646 | A1 | 1/2011 | Usey | |
| 2011/0043537 | A1* | 2/2011 | Dellon | G09B 23/28 345/647 |
| 2011/0230792 | A1 | 9/2011 | Sarig-Bahat | |
| 2012/0188285 | A1 | 7/2012 | Friedlander et al. | |
| 2012/0245492 | A1 | 9/2012 | Lee | |
| 2013/0009853 | A1 | 1/2013 | Hesselink et al. | |
| 2014/0121018 | A1 | 5/2014 | Burdea | |
| 2014/0282224 | A1 | 9/2014 | Pedley | |
| 2014/0282274 | A1 | 9/2014 | Everitt et al. | |
| 2015/0052481 | A1 | 2/2015 | Ronkainen | |
| 2015/0133206 | A1 | 5/2015 | Sarrafzadeh et al. | |
| 2015/0141773 | A1 | 5/2015 | Einav et al. | |
| 2015/0199917 | A1 | 7/2015 | French | |
| 2016/0038075 | A1 | 2/2016 | Burdea et al. | |
| 2016/0082319 | A1* | 3/2016 | Macri | G09B 19/003 434/257 |
| 2016/0262680 | A1 | 9/2016 | Martucci et al. | |
| 2017/0011210 | A1 | 1/2017 | Cheong et al. | |
| 2017/0025026 | A1 | 1/2017 | Ortiz Catalan | |
| 2017/0069223 | A1 | 3/2017 | Cramer et al. | |
| 2017/0188894 | A1 | 7/2017 | Chang et al. | |
| 2017/0206691 | A1 | 7/2017 | Harrises et al. | |
| 2018/0005443 | A1 | 1/2018 | Poulos et al. | |
| 2018/0096111 | A1 | 4/2018 | Wells et al. | |
| 2018/0117318 | A1* | 5/2018 | Milekovic | A61B 5/0036 |
| 2018/0151258 | A1 | 5/2018 | S Nchez Vives et al. | |
| 2018/0164995 | A1 | 6/2018 | Czupi | |
| 2018/0165854 | A1 | 6/2018 | Du | |
| 2018/0178008 | A1* | 6/2018 | Bouton | A61N 1/0551 |
| 2018/0206773 | A1 | 7/2018 | Yu et al. | |
| 2018/0301057 | A1 | 10/2018 | Hargrove et al. | |
| 2018/0336973 | A1* | 11/2018 | Tadi | G06T 19/003 |
| 2019/0030394 | A1 | 1/2019 | Orr | |
| 2019/0060708 | A1 | 2/2019 | Fung | |
| 2019/0065970 | A1 | 2/2019 | Bonutti et al. | |
| 2019/0088152 | A1* | 3/2019 | Adamovich | A61B 5/1128 |
| 2019/0209856 | A1* | 7/2019 | Segal | A61B 5/316 |
| 2019/0371028 | A1 | 12/2019 | Harrises et al. | |
| 2019/0378621 | A1 | 12/2019 | Ellison | |
| 2020/0135042 | A1 | 4/2020 | An et al. | |
| 2020/0253527 | A1 | 8/2020 | Ellison | |
| 2020/0269123 | A1 | 8/2020 | Sachs et al. | |
| 2021/0008410 | A1 | 1/2021 | Athanasiou et al. | |
| 2021/0035674 | A1 | 2/2021 | Volosin et al. | |

OTHER PUBLICATIONS

International Search Report and Written Opinion issued for PCT Application No. PCT/IB2019/053342, dated Aug. 1, 2019, 8 pages.

* cited by examiner

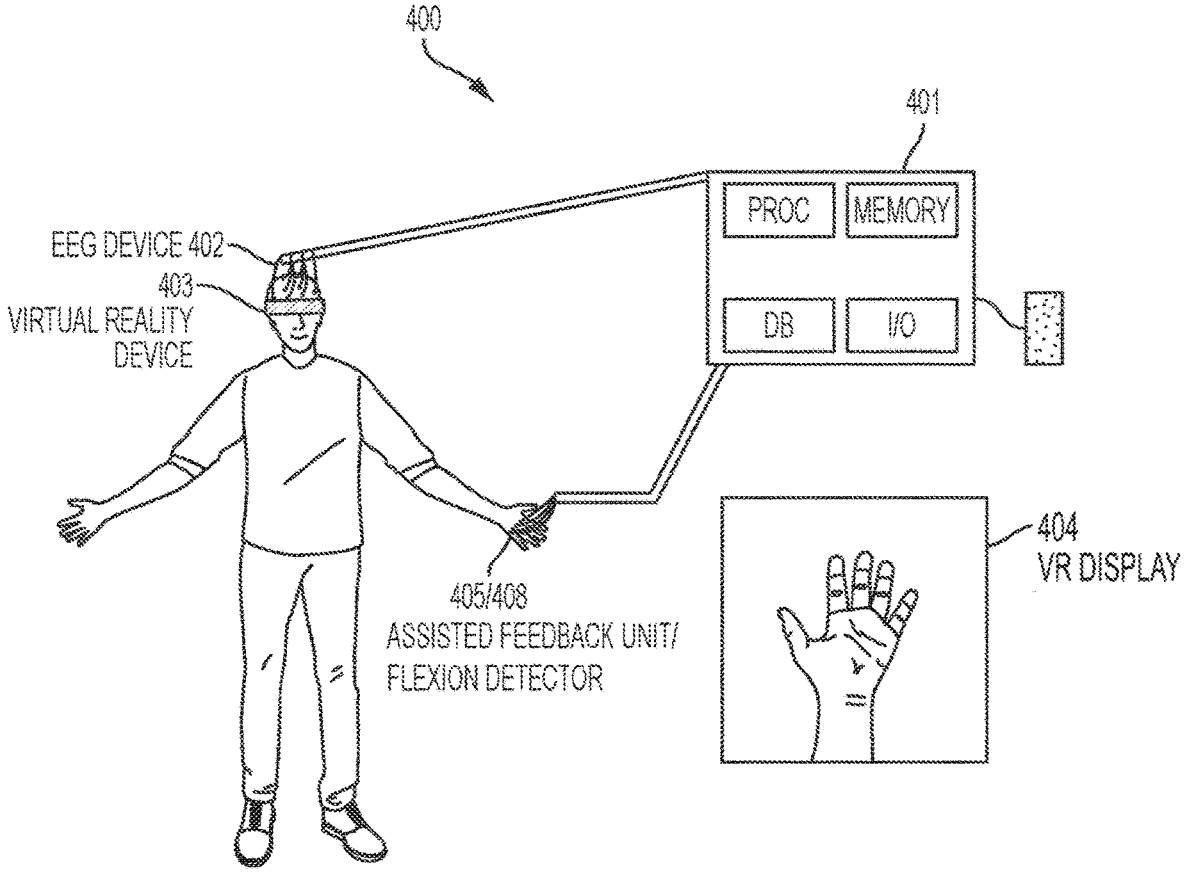
FIG. 4 (AMENDED)

SYSTEMS AND METHODS FOR NEURAL PATHWAYS CREATION/REINFORCEMENT BY NEURAL DETECTION WITH VIRTUAL FEEDBACK

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention relates generally to physical therapy technologies, and more particularly to systems for creating/reinforcing neural pathways by neural detection with virtual feedback.

BACKGROUND OF THE INVENTION

There are, unfortunately, many people in the world who suffer from debilitating conditions that cause partial or total loss of physical motor abilities. Some of these conditions include neurological disorders, brain injuries, muscular dystrophy, amyotrophic lateral sclerosis (ALS), and/or incomplete spinal cord injuries. In these situations, a patient may lose motor function of a hand, an arm, a leg, a finger, etc. due to the brain injury, and thus, the patient may not be able to move the affected limb or may have limited flexion. Oftentimes, the problem is in the injured part of the brain, and although the affected limb may not be damaged, the part of the brain controlling the motor function of the affected limb may not function. In these cases, it is possible for the motor function of the affected limb to be regained if new neural pathways associated with the particular motor functions are created in the patient's brain bypassing the injured portions of the brain. This is possible because of the principle of neuroplasticity, which refers to the ability of the brain to transfer brain activity associated with a given function to a different location, i.e., to create new neural pathways.

Several techniques have been developed that leverage the principle of neuroplasticity. One of those techniques is the mirror therapy (MT) technique. Mirror therapy utilizes a mirror-based illusion in which a healthy limb is perceived by the patient as the affected limb. Thus, a patient experiencing loss of motor function on the right hand may use the left hand in mirror therapy to provide the illusion that the right hand is moving, thereby tricking the patient's brain into thinking that the right hand is moving when it is actually not. This illusion stimulates creation of new pathways in the injured brain that are associated with motor functions of the affected limb. However, mirror therapy is wholly ineffectual where there is no healthy limb that can be used. Additionally, the effect of the mirror technique may be limited, as the patient may be fully aware that a mirror is being used to provide the illusion that the affected limb is moving. Additionally, this technique provides no means of assisted physical feedback that assists the affected limb in actually moving, and thus, the physical therapy duration may be long.

Virtual reality has also been used to immerse patients in a virtual environment, which may be navigated by the patient. The exposure to the created virtual environment may create stimuli in the patient's brain that may be associated with the virtual function. However, these techniques do not provide a robust system for physical therapy that seeks to create/reinforce new neural pathways associated with motor functions of an affected limb.

Thus, the current state of the art is technologically deficient and there are currently no mechanisms that are directed to physical therapy in which a neural pattern of a patient's brain is associated to a particular target action of an affected limb, and then providing a virtual representation of the target action when the neural pattern is detected, while the affected limb may not perform the target function.

BRIEF SUMMARY OF THE INVENTION

The present invention is directed to devices, systems, and methods that implement a technological solution for implementing therapeutic devices that create/reinforce neural pathways associated with a target motor function using neural pattern detection with virtual feedback. The systems, devices, and techniques disclosed herein may be used in physical therapy, where an affected limb may have limited motor function, or flexion, due to an injured part of the brain. Using the techniques of the present disclosure, a system may be provided that may allow a patient to create/reinforce new pathways associated with the lost motor function. Thus, a patient may be able to regain at least part of the lost motor function.

In one embodiment, a method of providing virtual feedback of a neural pattern to create a neural pathway corresponding to an action of an affected limb of a physical therapy patient with brain injury is provided. The method includes detecting the neural pattern and determining a target action associated with the neural pattern. The method also includes generating a virtual feedback including a virtual action corresponding to the target action. In some aspects, the virtual action may be performed in a virtual representation of the affected limb, where a brain injury of a user may partially or wholly prevent the affected limb from performing the target action. The method may also include causing the virtual representation of the affected limb to be positioned within the virtual environment such that the virtual representation of the affected limb may be presented to the physical therapy patient in lieu of the real-world presence of the affected limb. For example, in some embodiments, the position of the virtual representation within the virtual environment may correspond to the position of the affected limb in the real world. The method may further include performing the virtual action corresponding to the target action by the virtual representation of affected limb, such that the virtual action is presented to the physical therapy patient to simulate the target action in the real-world.

In other embodiments, a system for providing virtual feedback of a neural pattern to create a neural pathway corresponding to an action of an affected limb of a physical therapy patient with brain injury may be provided. The system may include a neural pattern detector configured to detect the neural pattern, and a controller communicatively coupled to the neural pattern detector. In some aspects, the controller and the neural pattern detector may configured for wired and/or wireless communications. The controller may be configured to determine a target action associated with the neural pattern and to generate a virtual feedback including a virtual action corresponding to the target action. In some aspects, the virtual action may be performed in a virtual representation of the affected limb, where a brain injury of a user may partially or wholly prevent the affected limb from performing the target action. The system may also include a virtual representation unit configured to generate a virtual representation of the affected limb and to present the virtual representation of the affected limb in a position within the virtual environment such that the virtual representation of the affected limb is presented to the physical therapy patient in lieu of the real-world presence of the affected limb. For example, in some embodiments, the position of the virtual representation within the virtual environment may correspond to the position of the affected limb in the real world. The virtual representation unit may also be configured to display the virtual action, corresponding to the target action, as being performed by the virtual representation of affected limb, such that the virtual action is presented to the physical therapy patient to simulate the target action in the real-world.

In yet another embodiment, an apparatus for providing virtual feedback of a neural pattern to create a neural pathway corresponding to an action of an affected limb of a physical therapy patient with brain injury may be provided. The apparatus may include a memory and at least one processor coupled to the memory. The at least one processor may be configured to detect the neural pattern and to determine a target action associated with the neural pattern. The at least one processor may also be configured to generate a virtual feedback including a virtual action corresponding to the target action. In some aspects, the virtual action may be performed in a virtual representation of the affected limb, where a brain injury of a user may partially or wholly prevent the affected limb from performing the target action. The at least one processor may also be configured to cause the virtual representation of the affected limb to be positioned within the virtual environment such that the virtual representation of the affected limb is presented to the physical therapy patient in lieu of the real-world presence of the affected limb. For example, in some embodiments, the position of the virtual representation within the virtual environment may correspond to the position of the affected limb in the real world. The at least one processor may be further configured to perform the virtual action corresponding to the target action by the virtual representation of affected limb, such that the virtual action is presented to the physical therapy patient to simulate the target action in the real-world.

In some embodiments, further functionality for training and learning may be provided. For example, systems in accordance with the present disclosure may provide functionality to determine a baseline measurement of a neural pattern of a patient that may be used to train the system to facilitate detection of neural patterns for a particular patient during operations. Additionally, a system in accordance with the present disclosure may include generation of physical feedback that includes an assisted physical action corresponding to the target action associated with the neural pattern, wherein the assisted physical action may be performed in the real-world environment. In aspects, the assisted physical action may be performed by an assisted physical feedback unit that may be configured to assist or to force movement of a target site by means of mechanical force, or to provide resistance to movement of the target site. In embodiments, the assisted physical action performed in the real-world may correspond to the virtual action performed in the virtual environment.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIG. 4 shows an example of operations implemented in system 400 in accordance with aspects of the present disclosure.

DETAILED DESCRIPTION OF THE INVENTION

Various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 1:
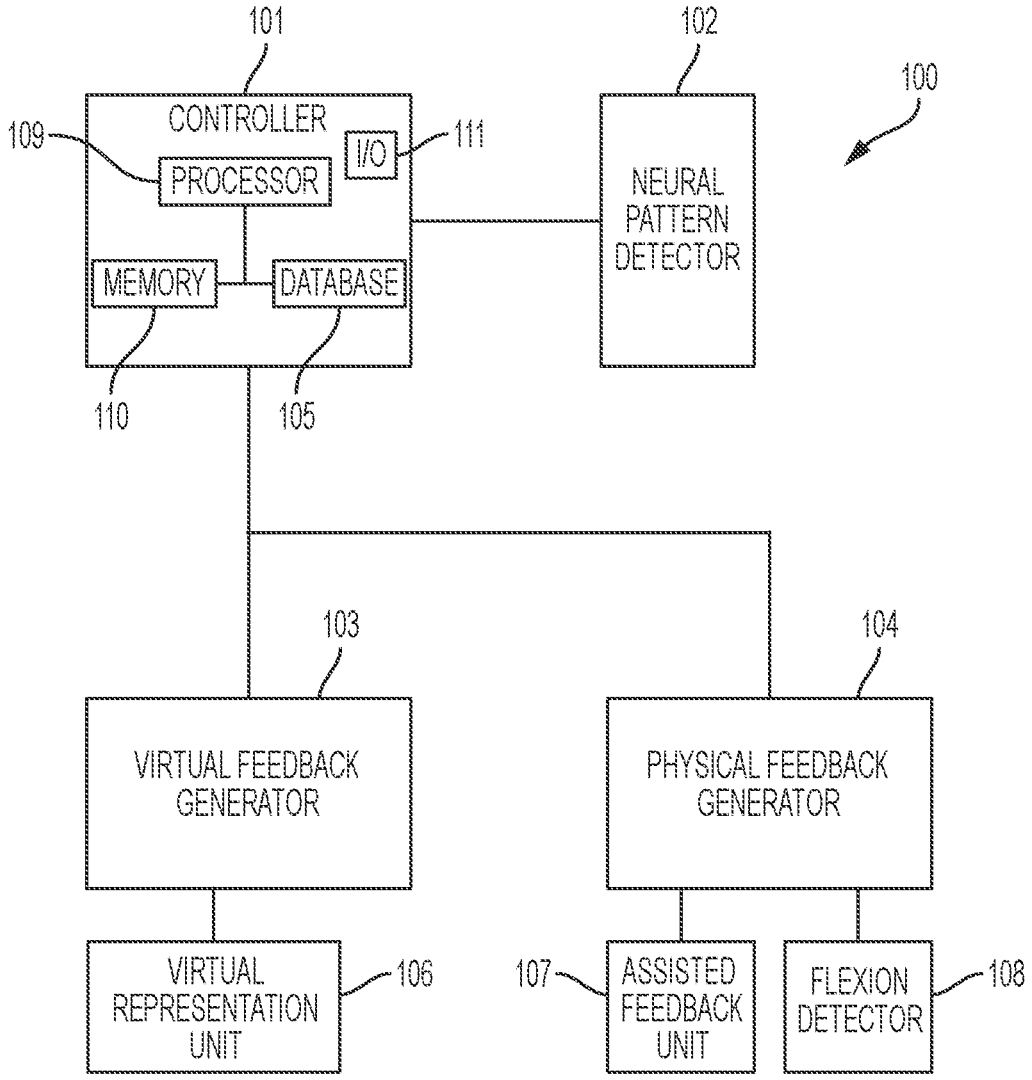
FIG. 1 shows system configured to perform operations in accordance with embodiments of the invention.

FIG. 1 illustrates a system 100 configured in accordance with embodiments of the present disclosure. The configuration of system 100 may facilitate operations for creating and/or reinforcing neural pathways associated with target actions by using neural pattern detection with various feedback techniques as described in embodiments of the present disclosure.

As shown in FIG. 1, system 100 may include controller 101, neural pattern detector 102, virtual feedback generator 103, physical feedback generator 104, database 105, virtual representation unit 106, assisted feedback unit 107, flexion detector 108, processor 109, memory 110, and input/output (I/O) unit 111. These components may cooperatively operate to provide functionality in accordance with the discussion herein. In embodiments, as will be discussed in more detail below, the operations of system 100 may include a training and learning process, and an operational process. The training and learning process may facilitate configuring and setting up system 100 for operational use, and may include operations for determining baseline neural patterns, for identifying and/or determining neural patterns associated with particular target actions, and/or for storing those neural patterns associated with the target actions. The operational process may include operations for detecting a neural pattern, for determining a target action associated with the neural pattern, for providing feedback, and/or for controlling the feedback based on flexion measurements.

It is noted that as used herein, the term flexion may relate to motion related to a user's motor function. In some cases, flexion information may be provided by a motion associated with motor function (e.g., opening/closing of a fist, extending/contracting an arm, opening/closing jaw, etc.) which may be detected via motion detectors. In these cases, the movement caused by the motor function provides information about the flexion related to the motor function.

It is further noted that as used herein, a neural pattern may refer to a pattern corresponding to a pattern of activity in the brain. In some aspects, the pattern of activity may be produced by electrical activity, magnetic activity, blood flow activity, and/or other biological or metabolic activity within the brain, or a combination thereof. A neural pattern may also be referred to as a brainwave pattern, neural oscillations pattern, etc. The neural pattern may be associated with a particular thought, which may itself be associated with a desired target action. This neural pattern may be detected in accordance with aspects of the present disclosure.

As used herein, a target action may refer to an intended or desired action related to a patient's motor function. For example, for a therapy patient with limited hand flexion, a target action may refer to a desired action of closing the hand, or to a desired action of opening the hand. In some aspects, the target action may be an action related to a motor function that a patient may not be able to perform, or may be limited, due to the brain injury, although the patient may desire and/or intend to perform the action. In embodiments discussed herein, the target action may be associated with a particular neural pattern.

It is also noted that the discussion herein focuses on operations with respect to an affected limb. However, it will be appreciated that the present disclosure is also applicable to situations in which the motor function affected is related to a site that may not necessarily be referred to as a limb, e.g., a facial muscle. Thus, it will be appreciated that the devices and methods discussed in the present disclosure may also be applicable when the affected motor function is associated with any muscle or muscle group of a patient.

In accordance with embodiments of the present disclosure, neural pattern detector 102 may include a detector configured to detect a patient's neural pattern and to provide the detected neural pattern to controller 101. In some aspects, neural pattern detector 102 may be configured to detect a pattern of activity corresponding to one or more of electrical activity, magnetic activity, blood flow activity, and/or other biological and metabolic activity within the brain. In embodiments, neural pattern detector 102 may include at least one of an electroencephalography (EEG) detector, a magnetoencephalography (MEG) detector, a positron-emission tomography (PET) detector, a magnetic resonance imaging (MRI) detector, a functional MRI (fMRI) detector, a computed tomography (CT) detector, a single-photon emission CT (SPECT) detector, a functional Near-Infrared Spectroscopy (fNIR) detector, and/or any detector configured to detect a corresponding neural pattern. It is noted that the foregoing exemplary types of neural pattern detectors have been provided for purposes of illustration, rather than by way of limitation, and that neural pattern detector 102 may include other types of neural pattern detectors in accordance with aspects of the present disclosure.

In embodiments, neural pattern detector 102 may comprise an EEG having a plurality of electrodes configured to be placed on a patient's scalp and configured to detect the pattern of activity in the patient's brain. The electrodes may be placed in contact with the patient's scalp in pre-specified locations to obtain measurements from targeted areas of the brain. In some embodiments, neural pattern detector 102 may include a wearable cap or net into which electrodes are embedded, and which may be placed on top a patient's scalp. The number and/or location of electrodes in neural pattern detector 102 may be predetermined based on a desired resolution, or may be dynamically determined based on operational observations. For example, neural pattern detector 102 may be configured with any number of electrodes from 6 to 256 electrodes, depending on operational requirements. Alternatively, or additionally, the number of electrodes in neural pattern detector 102 may be determined based on measurements taken during operations. For example, it may be determined that neural pattern detector 102 may not be adequately detecting a neural pattern. In this case, the number of active electrodes in neural pattern detector 102 may be increased. In another example, it may be determined that neural pattern detector 102 is adequately detecting a neural pattern. In this other example, the number of electrodes in neural pattern detector 102 may be decreased without affecting the neural pattern detection operations. In embodiments, the number of electrodes in neural pattern detector 102 may be changed (increased or decreased) by activating or deactivating individual electrodes. It will be appreciated that deactivating electrodes, when appropriate, may decrease power consumption, which may result in power savings, especially in mobile applications.

It is noted that the neural pattern detected by neural pattern detector 102 may have certain characteristics, such as a frequency and an amplitude. Thus, a particular neural pattern may be characterized, and in some instances may be identified, by a particular frequency and a particular amplitude. In other embodiments, the neural pattern may be characterized by a digital pattern, such as a particular series or sequence of 0 and 1. In this manner, a neural pattern, once detected, may be analyzed to determine whether the neural pattern is associated to a previously determined neural pattern, or may be analyzed as part of a training and learning process to determine if a change in the target action neural pattern has occurred. Additionally, a detected pattern may be associated with a particular patient and may be stored with an indication of the association to the patient.

System 100 may include controller 101 configured to provide functionality in accordance with aspects of the present disclosure. In some embodiments, controller 101 may be implemented using a desktop computer, a laptop computer, a smartphone, a tablet computing device, a personal digital assistant (PDA), another type of wired and/or wireless computing device, or part thereof. Controller 101 may include processor 109, memory 110, and database 105. In embodiments, processor 109 may comprise a processor, a microprocessor, a controller, a microcontroller, a plurality of microprocessors, an application-specific integrated circuit (ASIC), an application-specific standard product (ASSP), or any combination thereof, and may be configured to execute instructions to perform operations in accordance with the disclosure herein. In some aspects, implementations of processor 109 may comprise code segments (e.g., software, firmware, and/or hardware logic) executable in hardware, such as a processor, to perform the tasks and functions described herein. In yet other aspects, processor 109 may be implemented as a combination of hardware and software.

In some aspects, processor 109 may be communicatively coupled to memory 110. Memory 110 may comprise read only memory (ROM) devices, random access memory (RAM) devices, one or more hard disk drives (HDDs), flash memory devices, solid state drives (SSDs), other devices configured to store data in a persistent or non-persistent state, or a combination of different memory devices. Memory 110 may store instructions that, when executed by processor 109, cause processor 109 to perform operations in accordance with the present disclosure.

In some embodiments, memory 110 may also be configured to facilitate storage operations. For example, memory 110 may comprise database 105 for storing previously determined or detected neural patterns, target actions, threshold values, user profile information, etc. In aspects, database 105 may be integrated into memory 110, or may be provided as a separate module. In yet other aspects, database 105 may be a single database, or may be a distributed database implemented over a plurality of database modules. Database 105 may be configured to store information for a plurality of patients. In some cases, the information may be used in training and learning operations, as discussed below.

It is noted that in some embodiments, controller 101 and neural pattern detector 102 may be implemented in a single device, rather than separate devices. For example, controller 101 and neural pattern detector 102 may be implemented as a single device that may be placed on a patient's head. In this example, the detection of the neural pattern and the processing and analysis may be performed by operations in the single device. In alternative embodiments, controller 101 and neural pattern detector 102 may be implemented as separate units, communicatively coupled to one another. As noted above, controller 101 and neural pattern detector 102 may configured for wired and/or wireless communications.

In embodiments, controller 101 may include I/O unit 111. In some embodiments, I/O unit may include a display, and may be configured to display a graphical user interface (GUI) structured to facilitate input and output operations in accordance with aspects of the present disclosure. 111 I/O unit 111 may be configured to accept input from users, such as a patient or a therapist that may be used to specify the affected motor function, the associated limb, the target action desired, particular motor function limitations of the patient, etc. Thus, for example, a therapist may use I/O unit 111 to specify a target action that the patient is to perform during therapy. In some embodiments, I/O unit 111 may be configured to provide output which may present, display, or reproduce the virtual environment. In these cases, a therapist may be able to monitor what the patient is perceiving in the virtual environment.

Controller 101 may be configured to receive a detected neural pattern from neural pattern detector 102, to analyze and process the detected neural pattern, and to drive feedback generation in accordance with the discussion herein. In some aspects, controller 101 may provide operations to facilitate a training and learning process, and operations to facilitate an operational process, as discussed in more detail below. Controller 101 may be configured to provide neural pattern information to virtual feedback generator 103 and/or to physical feedback generator 104.

In embodiments, controller 101 may analyze a detected pattern to determine whether the neural pattern is associated to a previously determined neural pattern. For example, controller 101 may compare a detected neural pattern with neural patterns stored in database 105 to determine if the detected neural pattern matches at least one of the stored neural patterns. In some embodiments, the matching may be based on a comparison of the frequency and/or amplitude of the detected neural pattern and the stored neural patterns. For example, controller 101 may compare the frequency of a neural pattern detected by neural pattern detector 102 with the frequency of each of the stored neural patterns in database 105 and, upon finding a match, controller 101 may determine that the detected neural pattern is associated with the matched neural pattern's target action.

System 100 may include virtual feedback generator 103. Virtual feedback generator 103 may comprise a processor configured to execute instructions to perform operations in accordance with the present disclosure. In embodiments, implementations of virtual feedback generator 103 may comprise code segments executable in hardware, such as a processor, to perform the tasks and functions described herein. In yet other aspects, virtual feedback generator 103 may be implemented as a combination of hardware and software.

As seen in FIG. 1, virtual feedback generator 103 may be communicatively coupled to controller 101, and may be configured to receive neural pattern information. Virtual feedback generator 103 may be configured to analyze the neural pattern information received from controller 101 and to generate a virtual feedback based on the neural pattern information received from controller 101. The virtual feedback may comprise a feedback signal that may be sent to virtual representation unit 106. The feedback signal may include a signal that drives virtual representation unit 106 to represent an action on a virtual representation, or virtual avatar, of the patient.

Virtual representation unit 106 may include a virtual reality device, an augmented reality device, a mixed reality device, a computer screen, a television screen, a projector, and/or any device configured to display a virtual representation of a patient, or a virtual representation of a portion or part of a patient. For example, virtual representation unit 106 may display a virtual avatar that may represent the patient undergoing physical therapy. In aspects, the virtual avatar may be configured with the physical attributes of the patient so that the patient may better relate to the virtual avatar. For example, the virtual avatar may include attributes similar to the patient's attributes, such as body shape, skin color, height, weight, hair color, age, gender, etc. In this cases, the virtual avatar may be associated with a particular patient and may be stored in database 105. In other aspects, the virtual avatar may be generic and may be similar regardless of the particular patient using the system.

In some embodiments, virtual representation unit 106 may be configured to display the virtual avatar, or a virtual limb, such that the position of the virtual limb within the virtual environment may correspond to the position of the corresponding physical limb of the patient in the real-world environment, and such that the patient may perceive the virtual limb as part of the patient. For example, a virtual avatar limb may be displayed within the virtual environment of virtual representation unit 106 such that the virtual avatar limb may be positioned in a location and arrangement corresponding to the position and arrangement of the real-world limb of the patient. In this case, the patient, while looking at the position within the virtual environment corresponding to the position where the real-world limb of the patient may be, may observe the virtual avatar limb instead. Thus, the patient may perceive any action represented in the virtual representation as an action performed by the patient and in this manner, the virtual feedback, represented as a virtual action, may be perceived as a patient's action, thereby contributing to the creation/reinforcement of neural pathways associated with the action.

In embodiments, the action to be represented in the virtual avatar may correspond to the desired target action discussed above. For example, the feedback signal may indicate to virtual representation unit 106 to represent the action of closing a hand into a fist on a virtual representation of a patient, e.g., the virtual avatar. In some aspects, the feedback signal may specify various parameters for the target action to be represented in the virtual avatar. For example, the feedback signal may specify the amount of flexion, the speed of the movement, and/or the force of the movement associated with the action. In the exemplary case of the target action being a closing of a hand, the associated feedback signal may specify how fast the hand is to be closed in the virtual representation, the force with which the hand is to be closed, and/or how much the hand is to be closed.

System 100 may include physical feedback generator 104. Physical feedback generator 104 may comprise a processor configured to execute instructions to perform operations in accordance with the present disclosure. In embodiments, implementations of physical feedback generator 104 may comprise code segments executable in hardware, such as a processor, to perform the tasks and functions described herein. In yet other aspects, physical feedback generator 104 may be implemented as a combination of hardware and software.

It should be noted that, although controller 101, virtual feedback generator 103, and physical feedback generator 104 are discussed herein a separate modules, in some embodiments, controller 101, virtual feedback generator 103, and physical feedback generator 104 may be part of a single module. For example, in some implementations, virtual feedback generator 103 and physical feedback generator 104 may be implemented as code segments executable in processor 109. Thus, it should be appreciated that the discussion of controller 101, virtual feedback generator 103, and physical feedback generator 104 as separate modules is for purposes of illustrating and emphasizing the functionality of the difference modules, but it should not be construed as limiting, with respect to their implementation, in any way.

As seen in FIG. 1, physical feedback generator 104 may be communicatively coupled to controller 101, and may be configured to receive neural pattern information from controller 101. Physical feedback generator 104 may be configured to analyze the neural pattern information received from controller 101 and to generate a physical feedback based on the neural pattern information received from controller 101. The physical feedback may comprise a physical feedback signal that may be sent to assisted feedback unit 107. The physical feedback signal may include a signal that drives assisted feedback unit 107 to perform an assisted action corresponding to the physical feedback.

Assisted feedback unit 107 may include a wearable device that may be placed on a target site associated with an affected motor function, such as a limb with limited flexion, and may be configured to assist or to force movement of the target site by means of mechanical force, or to provide resistance to movement of the target site. For example, assisted feedback unit 107 may include a glove, an arm or leg brace, or any other wearable device that may be placed upon a target site and may be configured to assist or force bending, twisting, flexing, extending, etc., of the target site. In some aspects, the mechanical means for assisting or forcing the movement may include motors, actuators, hydraulic actuators, pneumatic actuators, pressure-based actuators, etc. In some embodiments, assisted feedback unit 107 may include mechanical means for preventing the target site from being moved, thereby providing resistance training to be used during therapy to strengthen the target site.

In embodiments, the physical feedback signal may specify various parameters for the target action to be performed by assisted feedback unit 107. For example, the feedback signal may specify the amount of flexion, the speed of the movement, and/or the direction of the movement associated with the target action. In an exemplary case of a target action being a closing of a hand, the associated physical feedback signal may specify how fast the hand is to be closed, the direction of movement of the hand, and/or how much the hand is to be closed. In some embodiments, assisted feedback unit 107 may be configured to respond to the physical feedback signal from physical feedback generator 104 and to position, by use of the mechanical means, the target site to a position that may be specified by the physical feedback signal.

It is noted that, in some embodiments, the target action for assisted feedback unit 107 may correspond to a target action associated with virtual representation unit 106, and may be a similar action. For example, a physical feedback signal from physical feedback generator 104 derived from neural pattern information may specify a target action for closing a hand to be performed by assisted feedback unit 107. The same neural pattern information may be received by virtual feedback generator 103 and may result in a virtual feedback signal specifying a target action for closing a hand in the virtual avatar. Thus, a target action of closing a hand may be coordinately performed virtually and physically, and the patient may be able to perceive the action virtually or physically, due to the cooperative operation of system 100. Additionally, in some embodiments, the same target action may be performed differently in the virtual environment than in the physical environment. For example, where a target action of a target site, such as an affected limb, beyond a particular limit may be counter-indicated for a patient, the target action may be performed virtually with a set of parameter values, and may also be performed physically with a different set of parameter values. In an exemplary case of a target action being opening of a hand, the patient may experience pain when the hand is extended beyond, e.g., 10% of full flexion. In this example, after detecting and analyzing a neural pattern, neural pattern information may be sent from controller 101 to virtual feedback generator 103 and physical feedback generator 104. Virtual feedback generator 103 may generate a virtual feedback signal specifying a 100% extension of the virtual avatar hand, and virtual representation unit 106 may display the virtual avatar hand opening with a 100% extension. In this same example, physical feedback generator 104 may generate a physical feedback signal specifying a 10% extension, and assisted feedback unit 107 may operate to physically extend to 10% extension of the patient's hand. Thus, in this example, although the physical extension of the patient's limb may be 10%, the virtual representation of the patient's hand may be extended to 100%. Therefore, the patient may perceive a 100% extension, while physically experiencing a 10% extension.

System 100 may also include flexion detector 108. Although in the embodiment shown in FIG. 1 flexion detector 108 is shown communicatively coupled to physical feedback generator 104, in some embodiments, flexion detector 108 may be communicatively coupled to controller 101, and may be configured to provide measurements with respect to a physical position and conformation of a target site. It is also noted that, although flexion detector 108 and assisted feedback unit 107 are shown as separate units, in some embodiments, flexion detector 108, may be physically or functionally integrated within assisted feedback unit 107. In embodiments, flexion detector 108 may be configured to be placed on a target site and may include sensors configured to measure conformation, location, movement, speed, velocity, tilt, position, force, etc., of the target site. For example, flexion detector 108 may be configured to take measurements with respect to a flexion status of a limb, including whether a limb has moved or may be moving, the speed of the movement, the force of the movement, the extent of the movement, etc. In this manner, the measurements taken by flexion detector 108 may indicate whether a limb is extended or contracted, how much the limb has extended or contracted, with what force the limb was extended or contracted, etc.

In some embodiments, the flexion measurements measured by flexion detector 108 may be provided to controller 101 and/or virtual feedback generator 103. In these embodiments, the flexion measurements may be used to modify the virtual representation of the limb. For example, the flexion measurements may indicate that a limb is extended to 10%, and the profile information may indicate that the patient has a maximum flexion of 20%. In this case, the virtual representation of the limb may be displayed as 50% extended, because 50% of 20% is 10%. These capabilities of flexion detector 108 may also allow modifying the virtual representation of the limb to reflect progress during therapy. For example, a patient, at the initial stages of therapy may only be capable of 10% flexion of an affected limb. In this case, during operation, a 10% flexion detected by flexion detector 108 may be determined to correspond to 100% flexion in the virtual avatar. Based on this, virtual feedback generator 103 may cause virtual representation unit 106 to display a virtual action of the virtual avatar limb of 100% flexion. At a subsequent time during therapy the flexion limit of the affected limb may be determined to have increased to 20% flexion. In this case, during operation, a 20% flexion detected by flexion detector 108 may be determined to correspond to 100% flexion in the virtual avatar, whereas a 10% flexion detected by flexion detector 108 may be determined to correspond to 50% flexion in the virtual avatar. Based on this, virtual feedback generator 103 may cause virtual representation unit 106 to display a virtual action of the virtual avatar limb of 100% flexion when the flexion detected by flexion detector 108 is 20%, and may cause virtual representation unit 106 to display a virtual action of the virtual avatar limb of 50% flexion when the flexion detected by flexion detector 108 is 10%.

Figure 2:
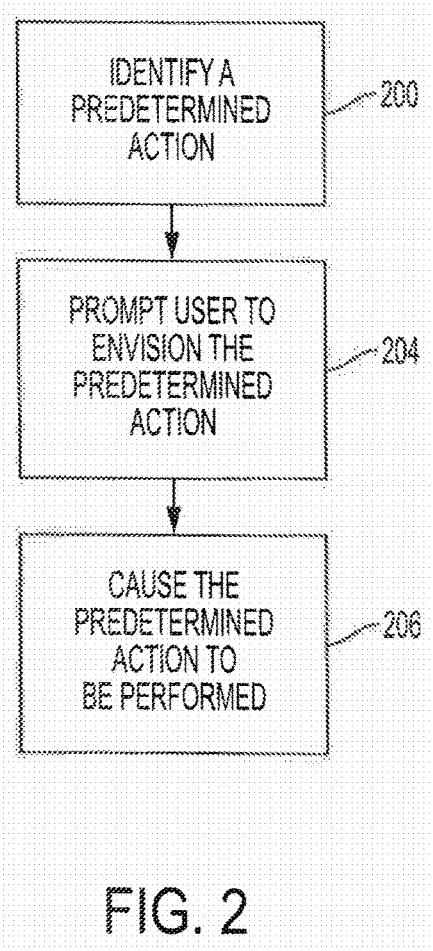
FIG. 2 shows a functional block diagram illustrating an example flow executed to implement aspects of the present disclosure.

As will be appreciated, these features allow a system implemented in accordance with the present disclosure to be configured to adapt the virtual feedback to the therapy progress. In some embodiments, the therapy progress may be determined via visual inspection by the therapist, or may be determined based on automatic measurements made by, e.g., flexion detector 108. In yet further embodiments, the modifications of the virtual feedback may be performed automatically, based on the determined therapy progress. As such, it should be appreciated that the feedback modifications may be adaptive in nature. For example, a therapist may determine that a patient has 10% motion at the beginning of therapy. In this case, the therapist may manually configure system 100 to specify the 10% motion of the patient. The system may then use the manual configuration to configure the virtual feedback such that 10% motion, as measured by the flexion detector, corresponds to 100% motion in the virtual representation. Additionally, Operations of system 100 to provide functionality in accordance with the present disclosure will now be discussed with respect to the flowcharts shown in FIGS. 2 and 3. FIG. 2 shows a diagram illustrating example blocks executed to implement one aspect of the present disclosure. The procedure according to this example aspect details steps for implementing a learning and training process in accordance with the present disclosure. At block 200, a predetermined action is identified. In some embodiments, the predetermined action may be a known action, and/or may be an action that is achievable. For example, the predetermined action may comprise moving a virtual ball from one position to another, or may comprise extending or contracting an unaffected limb of a patient.

At block [202] *204*, the patient is prompted to think, envision, or take the predetermined action as a desired target action to be performed, thereby stimulating neural activity in the patient's brain corresponding to a neural pattern associated with the predetermined action. At block 204, a neural pattern of the patient is detected. In some embodiments, the neural pattern may be detected using a neural pattern detector such as neural pattern detector 102. The detected neural pattern may be determined to be associated with the predetermined target action pattern and it may be stored in a database, such as database 105. In some aspects, the stored neural pattern may include an indication identifying the neural pattern as a training neural pattern.

At block 206, the system causes the predetermined action to be performed. In some embodiments, the predetermined action may be performed as a virtual action in virtual representation unit 106. In other aspects, e.g., when the predetermined action is a physical action by an unaffected limb of the patient, the patient might be prompted to perform the predetermined action.

In embodiments, system 100 may be configured with learning capabilities. For example, as noted above, database 105 may be used to store neural patterns from different patients. The stored neural patterns may be classified based on types of injuries, baseline neural patterns, type of target action associated with the neural pattern, learning context (e.g., training or operational), etc. Using these classifications, system 100, under control of controller 101, may learn particular characteristics of a neural pattern associated with a particular target action and may apply those characteristics to subsequently detected neural patterns to identify the associated target action. Thus, in embodiments using this hive learning, individual training of the system may be bypassed.

The learning capabilities of the system may also include determining progress during therapy. In these embodiments, for a particular patient, a detected neural pattern associated with a target action may be compared with a previously stored neural pattern associated with the target action for the patient. If a difference between the two neural patterns is present, controller 101 may analyze the difference (e.g., difference in amplitude) and may update the stored neural pattern when it is determined that the new value is more advantageous (e.g., greater amplitude in the detected neural pattern).

Figure 3:
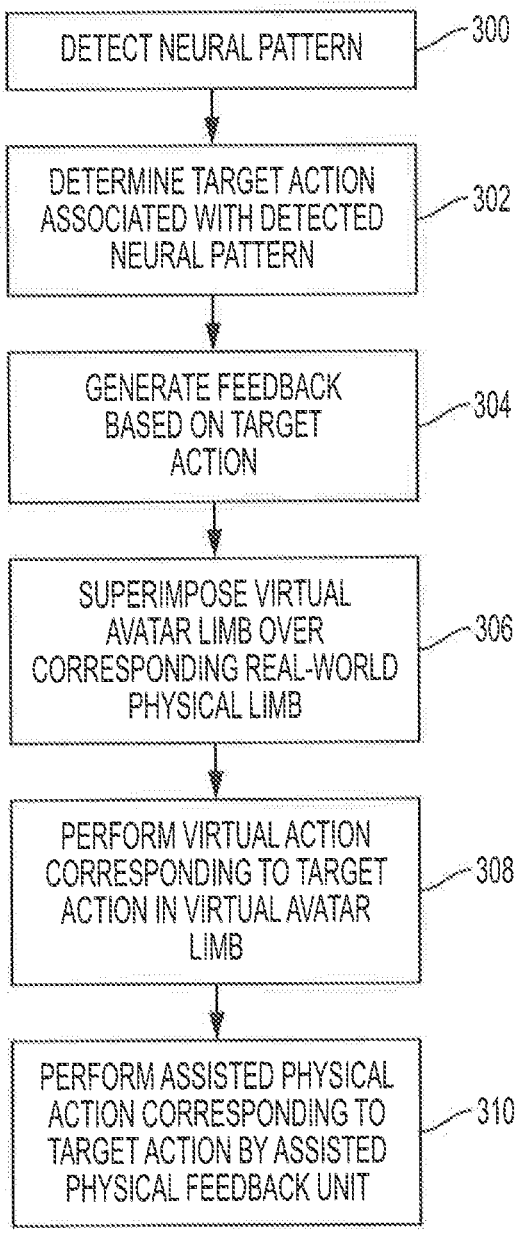
FIG. 3 shows another functional block diagram illustrating an example flow executed to implement aspects of the present disclosure.

FIG. 3 shows a diagram illustrating example blocks executed to implement one aspect of the present disclosure. The procedure according to this example aspect details steps for implementing an operational process in accordance with the present disclosure. The operational process may be performed during use of system 100 to provide neural pathway creation/reinforcement in accordance with aspects of the present disclosure. At block 300, a neural pattern of a therapy patient is detected. The neural pattern may be detected using a neural pattern detector such as neural pattern detector 102. In some embodiments, detecting the neural pattern at block 300 may be in response to prompting a patient to think or envision a target action, thereby stimulating neural activity in the patient's brain corresponding to a neural pattern associated with the target action. In other embodiments, the patient may not be prompted to think or envision a target action prior to detecting the neural pattern.

At block 302, a target action associated with the detected neural pattern is determined. In some embodiments, determining a target action associated with the detected neural pattern may include analyzing the detected pattern to determine whether the neural pattern is associated to a previously determined neural pattern. For example, a detected neural pattern may be compared with neural patterns stored in database 105 to determine if the detected neural pattern matches at least one of the stored neural patterns. In some embodiments, each of the stored neural patterns may be associated with a target action. The matching of the detected neural pattern with the stored neural patterns may be based on a comparison of the frequency and/or amplitude of the detected neural pattern and the stored neural patterns. For example, controller 101 may compare the frequency of the neural pattern detected by neural pattern detector 102 with the frequency of each of the stored neural patterns in database 105 until a match is detected. In other embodiments, the matching of the detected neural pattern with the stored neural patterns may be based on a comparison of the digital patterns, such as a particular series or sequence of 0's and 1's, of the stored neural patterns and the detected neural pattern. Upon finding a match for the detected neural pattern from the stored neural patterns, controller 101 may determine that the detected neural pattern is associated with the target action corresponding to the matched neural pattern. In some embodiments, the matching may not an exact match, and may instead be based on the detected neural pattern being within a threshold value of the matched neural pattern. For example, controller 101 may compare the frequency or digital pattern of the neural pattern detected by neural pattern detector 102 with the frequency or digital pattern of each of the stored neural patterns in database 105 and may find a match when the difference between the detected neural pattern and the matched neural pattern is within the threshold value. In embodiments, the matching process described may be used in the learning and training process, as discussed in further detail below.

In some embodiments, the matching of the detected neural pattern with the stored neural patterns may be based alternative or further signal processing to the comparing discussed above. For example, matching the detected neural pattern with the stored neural patterns may be based on pattern timing, pattern intensity, pattern duration, etc.

In some embodiments, the neural patterns stored in database 105 may include an indication of a patient with which the neural patterns are associated. In this manner, comparison operations to determine a target action associated with the detected neural pattern may focus the search for a match to only those neural patterns associated with the patient to which the detected neural pattern belongs. This allows for a faster and more targeted comparison operation.

At block 304, feedback is generated based on the target action. In embodiments the feedback may include at least one of virtual feedback and physical feedback. For example, controller 101 may provide neural pattern information that includes a target action to virtual feedback generator 103 and/or physical feedback generator 104. In this case, virtual feedback generator 103 and/or physical feedback generator 104 may generate a virtual feedback and/or a physical feedback, respectively, based on the target action indicated in the neural pattern information received from controller 101.

In embodiments, the virtual feedback may specify parameters for representing the target action in a virtual avatar limb. The parameters may include at least one of a flexion amount of the target action and a speed of movement to execute the target action in the virtual avatar limb. The virtual feedback may be provided to a virtual representation unit such as virtual representation unit 106. In embodiments, the physical feedback may specify parameters for performing the target action on an assisted feedback unit, such as assisted feedback unit 107. The parameters may include at least one of a flexion amount of the target action and a speed of movement to execute the target action by the assisted feedback unit. The physical feedback may be provided to the assisted feedback unit.

At block 306, the virtual avatar limb may be positioned within the virtual environment in a location and/or configuration corresponding to the location and/or configuration of real-world physical limb of the patient. In embodiments, the patient, while looking within the virtual environment at the position where the real-world physical limb of the patient may be, may observe the virtual avatar limb instead of the real-world physical limb. At block 308, a virtual action corresponding to the target action may be represented in the virtual avatar limb. In embodiments, the virtual action may be performed in accordance with the parameters specified in the virtual feedback information. It is again noted that in these embodiments, the patient may perceive the virtual avatar limb rather than the real-world physical limb and thus, may perceive the virtual action rather than any real-world physical action. As such, regardless of whether the real-world physical limb may perform the target action in response the patient's desired target action, the patient may perceive the desired target action as being performed. In this manner, even in cases where the patient has lost or has limited motor function of a physical limb due to brain injury, a system in accordance with the present disclosure may provide a means for creating and/or reinforcing neural pathways associated with a target action with respect to the lost motor function.

In some embodiments, block 310 may be optionally implemented to perform an assisted physical action corresponding to the target action. In embodiments, the assisted physical action may be performed in accordance with the parameters specified in the physical feedback information received from the physical feedback generator. In some embodiments, the assisted physical action may include driving an assisted feedback unit to assist the real-world physical limb of the patient to execute the target action. The assisted feedback unit may include mechanical means for causing the real-world physical limb to be moved. In some embodiments, the assisted feedback unit may include mechanical means for preventing the real-world physical limb from being moved, thereby providing resistance training to be used during therapy to strengthen the real-world physical limb.

In some aspects, the parameters in the virtual feedback specifying the virtual action and the parameters in the physical feedback specifying the assisted physical action may not be the same. In this case, the virtual action in the virtual avatar limb and the assisted physical action may be performed differently. For example, the virtual action may be performed with a first flexion value, and the assisted physical action may be performed with a second flexion value different that the first flexion value. In this manner, the virtual feedback and the physical feedback are decoupled to allow more flexibility during therapy. As such, as therapy progresses, the virtual and physical actions may be modified accordingly. For example, at the initial stages of therapy, a patient may be determined to have an initial profile that includes flexion limitations, such as amount and force of movement of the affected limb. In this case, the virtual action may be performed at 100% flexion value, while the physical action may be performed with a lesser flexion value. As therapy progresses, the flexion parameters used in the physical action may be increased accordingly.

FIG. 4 illustrates an example of operations implemented in system 400 in accordance with aspects of the present disclosure for providing functionality as discussed herein. In this example, during operation, a therapy patient suffering from limited motor function may be connected into system 400. In this example, the therapy patient may have lost, or may have limited flexion of the left hand, as illustrated in FIG. 4. The therapy patient may be connected to system 400 by placing neural pattern detector 402 upon the therapy patient's head, as described in more detail above. Neural pattern detector 402 may be the same as neural pattern detector 102 shown in FIG. 1, and in this example embodiment may be an EEG device. Virtual representation unit 403 may also be connected to the therapy patient. Virtual representation unit 403 may be a VR headset, or may be a virtual display *404* configured to display a virtual representation of the therapy patient's left hand. Optionally, assisted feedback unit 405 and flexion detector 408 may be placed upon the therapy patient's left hand. Assisted feedback unit 405 and flexion detector 408 may be the same as assisted feedback unit 107 and flexion detector 108 shown in FIG. 1.

In this example, neural pattern detector 402, virtual representation unit 403, assisted feedback unit 405, and flexion detector 408 may be communicatively coupled to controller 401, which may be the same as controller 101 of FIG. 1. In some embodiments, the communication between controller 401, neural pattern detector 402, virtual representation unit 403, assisted feedback unit 405, and flexion detector 408 may be via a wired connection. In other embodiments, each of controller 401, virtual representation unit 403, neural pattern detector 402, assisted feedback unit 405, and flexion detector 408 may be configured for wireless communication and, in this cases, communications between the different components may be wireless communications. Further, in some embodiments, assisted feedback unit 405 and flexion detector 408 may be implemented as a single unit, such as haptic glove.

In one example case, the therapist may select a training process that may be configured to train system 400 to facilitate detection of neural patterns from the therapy patient by calibrating the patient to the system. In this case, the system may prompt the therapy patient to envision a particular action, e.g., moving a displayed object to a particular position, a particular distance, or in a particular direction. The system may then, using neural pattern detector 402, detect the therapy patient's neural pattern as the therapy patient envisions the particular action, while the system virtually performs the particular action and presents it to the therapy patient via the virtual representation unit 403. These operations may be repeated to ensure that the neural pattern detected in response to the therapy patient's brain activity related to the envisioning of the particular action is consistent. Further additional training operations may be performed. These further training operations may include prompting the therapy patient to move additional, or different displayed objects, or may include prompting the therapy patient to perform an action that is not affected by the limited motor function (e.g., closing the therapy patient's right hand into a fist, where the motor function of the right hand is not affected). In this manner, the system may determine that the system is able to detect a neural pattern associated with a particular action with consistency and may be considered to be trained.

After training, the therapist may specify a target action. In embodiments, the therapist may enter a desired target action using an I/O unit, such as I/O unit 111 of FIG. 1, configure to accept an input. In this example, the target action may include closing the left hand into a fist. In some embodiments, the therapist may specify flexion limits of the therapy patient's left hand, which may be used to determine the flexion limits of the virtual and/or physical feedback.

The therapy patient may be prompted to envision, think, or perform the target action, and the patient may do so in response. This may cause brain activity corresponding to the target action in the therapy patient's brain, which may be detected as a neural pattern by neural pattern detector 402. The neural pattern may be provided to controller 401. Controller 401 may determine that the neural pattern detected corresponds to the target action. In response to this, controller may generate a virtual feedback signal, and optionally a physical feedback signal. The feedback signals may specify an action, corresponding to the target action, to be performed in a respective feedback unit. For example, the virtual feedback signal may specify a virtual action to be performed in virtual representation unit 403 corresponding to closing the left hand within the virtual environment provided by virtual representation unit 403. In an additional example, the physical feedback signal may specify a physical action to be performed in assisted feedback unit 405 corresponding to closing the left hand.

In response to the corresponding signals, a target action may be performed in the corresponding environment. For example, within the virtual environment provided by virtual representation unit 403, the therapy patient's virtual left hand may be closed into a fist, in accordance with the feedback signal. In some embodiments, the virtual left hand may be positioned within the virtual environment such that the patient's virtual left hand is presented to the physical therapy patient in lieu of the therapy patient's real-world left hand. In this case, the therapy patient may perceive the simulated virtual action as if it were being performed by the patient's real-world hand in the real world environment. In this manner, neural pathways associated with the target action of closing the left hand may be created and/or reinforced in the therapy patient's brain.

Optionally, and in response to the physical feedback signal, an assisted physical action may be performed by assisted feedback unit 405, in the real-world environment, corresponding to closing the left hand. For example, assisted feedback unit 405 may apply mechanical force or resistance upon the therapy patient's left hand in order to assist or force the therapy patient's left hand in performing the closing action. In aspects, the assisted physical action may be performed within flexion limits associated with the therapy patient's. Thus, when closing the therapy patient's beyond a particular limit may be counter indicated, the patient's left hand may not be fully closed, but may be closed to within those limits. In some cases, the limits may be increased as therapy progresses in order to ensure that the patient's flexion is improving.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Skilled artisans will also readily recognize that the order or combination of components, methods, or interactions that are described herein are merely examples and that the components, methods, or interactions of the various aspects of the present disclosure may be combined or performed in ways other than those illustrated and described herein.

Functional blocks and modules in FIGS. 1-3 may comprise processors, electronics devices, hardware devices, electronics components, logical circuits, memories, software codes, firmware codes, etc., or any combination thereof. Consistent with the foregoing, various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal, base station, a sensor, or any other communication device. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. Computer-readable storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, a connection may be properly termed a computer-readable medium. For example, if the software is transmitted from a website, server, or other remote source using a coaxial cable, fiber optic cable, twisted pair, or digital subscriber line (DSL), then the coaxial cable, fiber optic cable, twisted pair, or DSL, are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of providing virtual feedback of a neural pattern to create a neural pathway corresponding to an action of an affected limb of a physical therapy patient with brain injury, the method comprising:

detecting a first neural pattern in response to the physical therapy patient attempting to perform a predefined training action, the first neural pattern detected using sensors in contact with the head of the physical therapy patient;

determining the first neural pattern to be associated with the predefined training action;

storing the first neural pattern;

detecting a second neural pattern in response to the physical therapy patient attempting to perform a target action, the second neural pattern is detected using the sensors in contact with the head of the physical therapy patient;

determining the target action associated with the second neural pattern, wherein determining the target action includes comparing the first neural pattern with the second neural pattern;

in response to a positive comparison, generating a virtual feedback including a virtual action corresponding to the target action, wherein the virtual action is to be performed in a virtual representation of the affected limb, and wherein the brain injury prevents the affected limb from performing the target action;

causing the virtual representation of the affected limb to be superimposed over a real-world presence of the affected limb such that the virtual representation of the affected limb is presented to the physical therapy patient in lieu of the real-world presence of the affected limb;

*determining a flexion limit of the affected limb for the physical therapy patient;* performing the virtual action corresponding to the target action in the virtual representation of affected limb, such that the virtual action is presented to the physical therapy patient in lieu of the target action in the real-world; and

*measuring a conformation of the affected limb during the performing the virtual action, wherein performing the virtual action in the virtual representation of the affected limb is based on the flexion limit and the measured conformation, wherein a flexion of the virtual representation of affected limb is determined based on a ratio of the measured conformation to the flexion limit.*

[2. The method of claim 1, further comprising:

generating a physical feedback including a physical action corresponding to the target action, wherein the physical action is to be performed by an assistive unit configured to assist the affected limb in performing the physical action;

providing the physical feedback to the assistive unit; and performing, by the assistive unit, the physical action corresponding to the target action.]

[3. The method of claim 2, wherein the virtual feedback includes a first set of parameters for the performing the virtual action, and wherein the physical feedback includes a second set of parameters for the performing the physical action, and wherein the performing the virtual action is in accordance with the first set of parameters, and the performing the physical action is in accordance with the second set of parameters.]

[4. The method of claim 3, wherein the first set of parameters and the second set of parameters are different.]

5. The method of claim 1, wherein the virtual feedback includes a set of parameters for the performing the virtual action, and wherein the performing the virtual action is in accordance with the set of parameters.

6. The method of claim [1] *5*, wherein the set of parameters includes at least one of: amount of flexion of the virtual representation of the affected limb for the target action, a speed of the target action, and a force of the target action.

7. The method of claim 1, wherein the determining the target action associated with the second neural pattern includes:

determining that the second neural pattern matches the first neural pattern; and determining that the second neural pattern is associated with the action corresponding to the first neural pattern.

8. The method of claim 7, wherein the comparing includes comparing at least one of a frequency and an amplitude of the second neural pattern with a corresponding at least one of a frequency and an amplitude of the first neural pattern.

9. The method of claim 7, wherein the first neural pattern includes an indication of a patient with which the first neural pattern is associated, and wherein the comparing includes comparing the second neural pattern with [only neural patterns of] the first neural pattern *only if the first neural pattern is* associated with the physical therapy patient *based on the indication of the patient with which the first neural pattern is associated.*

[10. The method of claim 1, further including:

measuring a conformation of the affected limb during the performing the virtual action; and based on the measured conformation, automatically modifying the virtual representation of the affected limb to perform the target action.]

[11. The method of claim 10, wherein the modifying includes:

determining a flexion limit of the affected limb for the physical therapy patient; and performing the virtual action in the virtual representation of affected limb based on the flexion limit and the measured conformation, wherein a flexion of the virtual representation of affected limb is determined based on a ratio of the measured conformation to the flexion limit.]

12. A system for providing virtual feedback of a neural pattern to create a neural pathway corresponding to an action of an affected limb of a physical therapy patient with brain injury, the system comprising:

a neural pattern detector configured to detect neural activity in a brain of the physical therapy patient, the neural pattern detector configured to:

detect a first neural pattern in response to the physical therapy patient attempting to perform a predefined training action;

detect a second neural pattern in response to the physical therapy patient attempting to perform a target action;

a controller communicatively coupled to the neural pattern detector, the controller configured to:

determine the first neural pattern to be associated with the predefined training action;

determine the target action associated with the second neural pattern, wherein the determining the target action includes comparing the first neural pattern with the second neural pattern;

in response to a positive comparison, generate a virtual feedback including a virtual action corresponding to the target action, wherein the virtual action is to be performed in a virtual representation of the affected limb, and wherein the brain injury prevents the affected limb from performing the target action;

a virtual representation unit configured to:

generate a virtual representation of the affected limb;

superimpose the virtual representation of the affected limb over a real-world presence of the affected limb such that the virtual representation of the affected limb is presented to the physical therapy patient in lieu of the real-world presence of the affected limb; [and]

display the virtual action corresponding to the target action in the virtual representation of affected limb, such that the virtual action is presented to the physical therapy patient in lieu of the target action in the real-world; *and*

*a flexion detector configured to:*

*obtain measurements associated with a flexion status of the affected limb for the physical therapy patient, wherein the controller is further configured to determine a flexion limit of the affected limb for the physical therapy patient based on the measurements associated with the flexion status; and*

*measure a conformation of the affected limb during the display of the virtual action, wherein displaying the virtual action in the virtual representation of the affected limb is based on the flexion limit and the measured conformation, wherein a flexion of the virtual representation of affected limb is determined based on a ratio of the measured conformation to the flexion limit.*

[13. The system of claim 12, wherein the controller is further configured to generate a physical feedback including a physical action corresponding to the target action, and further comprising:

an assisted feedback unit configured to assist the affected limb in performing the physical action, and further configured to:

receive the physical feedback from the controller; and perform the physical action corresponding to the target action.]

[14. The system of claim 13, wherein the virtual feedback includes a first set of parameters for the performing the virtual action, and wherein the physical feedback includes a second set of parameters for the performing the physical action, and wherein the performing the virtual action is in accordance with the first set of parameters, and the performing the physical action is in accordance with the second set of parameters.]

[15. The system of claim 14, wherein the first set of parameters and the second set of parameters are different.]

16. The system of claim 12, wherein the virtual feedback includes a set of parameters for the performing the virtual action, and wherein the performing the virtual action is in accordance with the set of parameters.

17. The system of claim [12]*16*, wherein the set of parameters includes at least one of: amount of flexion of the virtual representation of the affected limb for the target action, a speed of the target action, and a force of the target action.

18. The system of claim 12, further comprising a database for storing at least the first neural pattern, and wherein the configuration of the controller to determine the target action associated with the second neural pattern includes configuration of the controller to:

determine that the second neural pattern matches the first neural pattern; and determine that the second neural pattern is associated with the action corresponding to the first neural pattern.

19. The system of claim 18, wherein the configuration of the controller to compare includes configuration of the controller to compare at least one of a frequency and an amplitude of the second neural pattern with a corresponding at least one of a frequency and an amplitude of the first neural pattern.

20. An apparatus for providing virtual feedback of a neural pattern to create a neural pathway corresponding to an action of an affected limb of a physical therapy patient with brain injury, the apparatus comprising:

a memory; and at least one processor coupled to the memory, the at least one processor configured to:

detect a first neural pattern in response to the physical therapy patient attempting to perform a predefined training action, the first neural pattern detected using sensors in contact with the head of the physical therapy patient;

determine the first neural pattern to be associated with the predefined training action;

store the first neural pattern;

detect a second neural pattern in response to the physical therapy patient attempting to perform a target action, the second neural pattern is detected using the sensors in contact with the head of the physical therapy patient;

determine the target action associated with the second neural pattern, wherein in determining the target action the at least one processor is further configured to compare the first neural pattern with the second neural pattern;

in response to a positive comparison, generate a virtual feedback including a virtual action corresponding to the target action, wherein the virtual action is to be performed in a virtual representation of the affected limb, and wherein the brain injury prevents the affected limb from performing the target action;

cause the virtual representation of the affected limb to be superimposed over a real-world presence of the affected limb such that the virtual representation of the affected limb is presented to the physical therapy patient in lieu of the real-world presence of the affected limb; and

*determine a flexion limit of the affected limb for the physical therapy patient;* perform the virtual action corresponding to the target action in the virtual representation of affected limb, such that the virtual action is presented to the physical therapy patient in lieu of the target action in the real-world*;* and

*measure a conformation of the affected limb during the performing the virtual action, wherein performing the virtual action in the virtual representation of the affected limb is based on the flexion limit and the measured conformation, wherein a flexion of the virtual representation of affected limb is determined based on a ratio of the measured conformation to the flexion limit.*

* * * * *